(12) United States Patent
Mackovjak

(10) Patent No.: US 12,337,211 B2
(45) Date of Patent: Jun. 24, 2025

(54) JUMP HEIGHT MEASURING DEVICE AND METHOD OF USE

(71) Applicant: Paul V. Mackovjak, Huntsville, AL (US)

(72) Inventor: Paul V. Mackovjak, Huntsville, AL (US)

( * ) Notice: Subject to any disclaimer, the term of this patent is extended or adjusted under 35 U.S.C. 154(b) by 132 days.

(21) Appl. No.: 18/376,061

(22) Filed: Oct. 3, 2023

(65) Prior Publication Data
US 2025/0108256 A1 Apr. 3, 2025

(51) Int. Cl.
A63B 24/00 (2006.01)
A63B 6/00 (2006.01)
A63B 71/06 (2006.01)

(52) U.S. Cl.
CPC .......... A63B 24/0062 (2013.01); A63B 6/00 (2013.01); A63B 71/0622 (2013.01); A63B 2220/20 (2013.01); A63B 2220/58 (2013.01); A63B 2220/805 (2013.01); A63B 2220/808 (2013.01); A63B 2220/833 (2013.01); A63B 2244/087 (2013.01)

(58) Field of Classification Search
CPC ............ A63B 24/0062; A63B 6/00; A63B 71/0622; A63B 2220/20; A63B 2220/58; A63B 2220/805; A63B 2220/808; A63B 2220/833; A63B 2244/087
See application file for complete search history.

(56) References Cited

U.S. PATENT DOCUMENTS

| | | | |
|---|---|---|---|
| 5,897,457 A * | 4/1999 | Mackovjak | A63B 24/00 482/3 |
| 9,855,484 B1 * | 1/2018 | Matak | A61B 5/0022 |
| 11,478,680 B1 * | 10/2022 | Frederick | G01S 17/08 |
| 12,115,428 B1 * | 10/2024 | Anton | A63B 69/0071 |
| 2012/0023163 A1 * | 1/2012 | Mangold | A63B 69/00 709/203 |
| 2012/0130514 A1 * | 5/2012 | Homsi | A63B 69/002 700/91 |
| 2012/0178587 A1 * | 7/2012 | Hofeldt | A63B 69/0071 482/15 |
| 2015/0153374 A1 * | 6/2015 | Balakrishnan | G16H 20/30 702/178 |
| 2017/0144052 A1 * | 5/2017 | Liang | A63B 5/11 |
| 2017/0284805 A1 * | 10/2017 | Zihajehzadeh | G06V 40/23 |
| 2019/0362140 A1 * | 11/2019 | Selivanau | A63B 24/0062 |
| 2020/0205720 A1 * | 7/2020 | Wagner | A63B 71/0622 |

(Continued)

Primary Examiner — Sundhara M Ganesan

(57) ABSTRACT

A jump height measuring device for measuring vertical jump height of a user includes a detector and a microphone, which are communicatively engaged to a microcontroller. The detector is positionable on a surface so it can detect feet of a user upon the surface and communicate a first signal to the microcontroller upon the feet leaving the surface. The microphone is attached to a landing mat, which is positionable on the surface proximate to the detector. The microphone detects a sound of the feet of the user landing upon the landing mat and communicates a second signal to the microcontroller. The microcontroller is programmed to calculate a height of a jump based upon a difference in time between receipt of the first signal and receipt of the second signal. The device also can be used as a timer and to assess Explosive Leg Power Force and response time.

19 Claims, 9 Drawing Sheets

(56) References Cited

U.S. PATENT DOCUMENTS

| | | | |
|---|---|---|---|
| 2020/0230486 A1* | 7/2020 | Shau | A63B 71/0622 |
| 2022/0266080 A1* | 8/2022 | Mervis | A63B 71/0622 |
| 2022/0305337 A1* | 9/2022 | Kolen | A43B 3/34 |
| 2022/0308082 A1* | 9/2022 | Kolen | A43B 5/00 |
| 2022/0392222 A1* | 12/2022 | Nakamura | A63B 71/06 |
| 2022/0394322 A1* | 12/2022 | Nakamura | A63B 71/06 |
| 2023/0021999 A1* | 1/2023 | Kipp | A63B 23/0211 |
| 2024/0001195 A1* | 1/2024 | Wang | A63B 24/0062 |
| 2024/0033575 A1* | 2/2024 | Kim | A63B 24/0062 |
| 2024/0238647 A1* | 7/2024 | Graham | A63B 24/0062 |

* cited by examiner

JUMP HEIGHT MEASURING DEVICE AND METHOD OF USE

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to performance measuring devices and more particularly pertains to a new performance measuring device for measuring vertical jump height of a user. While such performance measuring devices are known in the prior art, they are bulky and not readily transportable, as may be desirable for users who use such devices in their work and who travel for their work, such as coaches, trainers, or the like. Thus, a need for a compact and easy to transport device for measuring vertical jump heights still exists.

(2) Description of Related Art Including Information Disclosed Under 37 CFR 1.97 and 1.98

The prior art relates to performance measuring devices. One such prior art device for measuring vertical jump heights is claimed in U.S. Pat. No. 5,897,457, the sole inventor of which is one of the inventors of this invention. The device claimed in U.S. Pat. No. 5,897,457 comprised a pressure plate, which was of significant mass and size, which, along with other required components, rendered it difficult or impossible to transport, particularly upon aircraft. The prior art does not teach such a compact and transportable device, nor does it teach such a device wherein completion of a vertical jump is detected by a microphone.

(h) BRIEF SUMMARY OF THE INVENTION

An embodiment of the disclosure meets the needs presented above by generally comprising a detector and a microphone, which are communicatively engaged to a microcontroller. The detector, typically a pressure sensor or a proximity sensor, is positionable on a surface such that is can detect feet of a user upon the surface and is configured to communicate a first signal to the microcontroller upon the feet of the user leaving the surface. The microphone is attached to a landing mat, which is positionable on the surface proximate to the detector. The microphone is configured to detect a sound of the feet of the user landing upon the landing mat and to communicate a second signal to the microcontroller. The microcontroller is programmed to calculate a height of a jump based upon a difference in time between receipt of the first signal and receipt of the second signal.

Another embodiment of the disclosure includes a method of measuring vertical jump height of a user. The method entails providing the jump height measuring, according to the disclosure above. Steps of the method include positioning the detector and the landing mat on the surface, positioning one's feet such that they are detected by the detector, jumping from the surface, landing on the landing mat, and calculation by the microcontroller of the height of the jump.

Generally then, the purpose of this new invention the is to decrease the weight compared to existing jump systems to measure a vertical jump height of an athlete. Older systems required a handheld computer and a large, steel-plated rubber mat enclosed in rubber, and had a weight of over 25 pounds. The disclosure herein describes a system having a weight of less than 2 pounds. It typically will consist of a handheld computer, light weight rubber mat, tactile switch, and a vibration/sound sensor. It is also more accurate than prior devices as the reaction time of a tactile and sound switch is less than 5 msec, whereas prior art steel plated rubber mats have a reaction time of over 10 msec. This is important since an error of 10 msec in timing results in over one inch in vertical. Thus, aside from the ease of traveling with the disclosed device, such as on an airplane, the disclosed device provides for more accurate readings.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(j) DETAILED DESCRIPTION OF THE INVENTION

Figure 1:
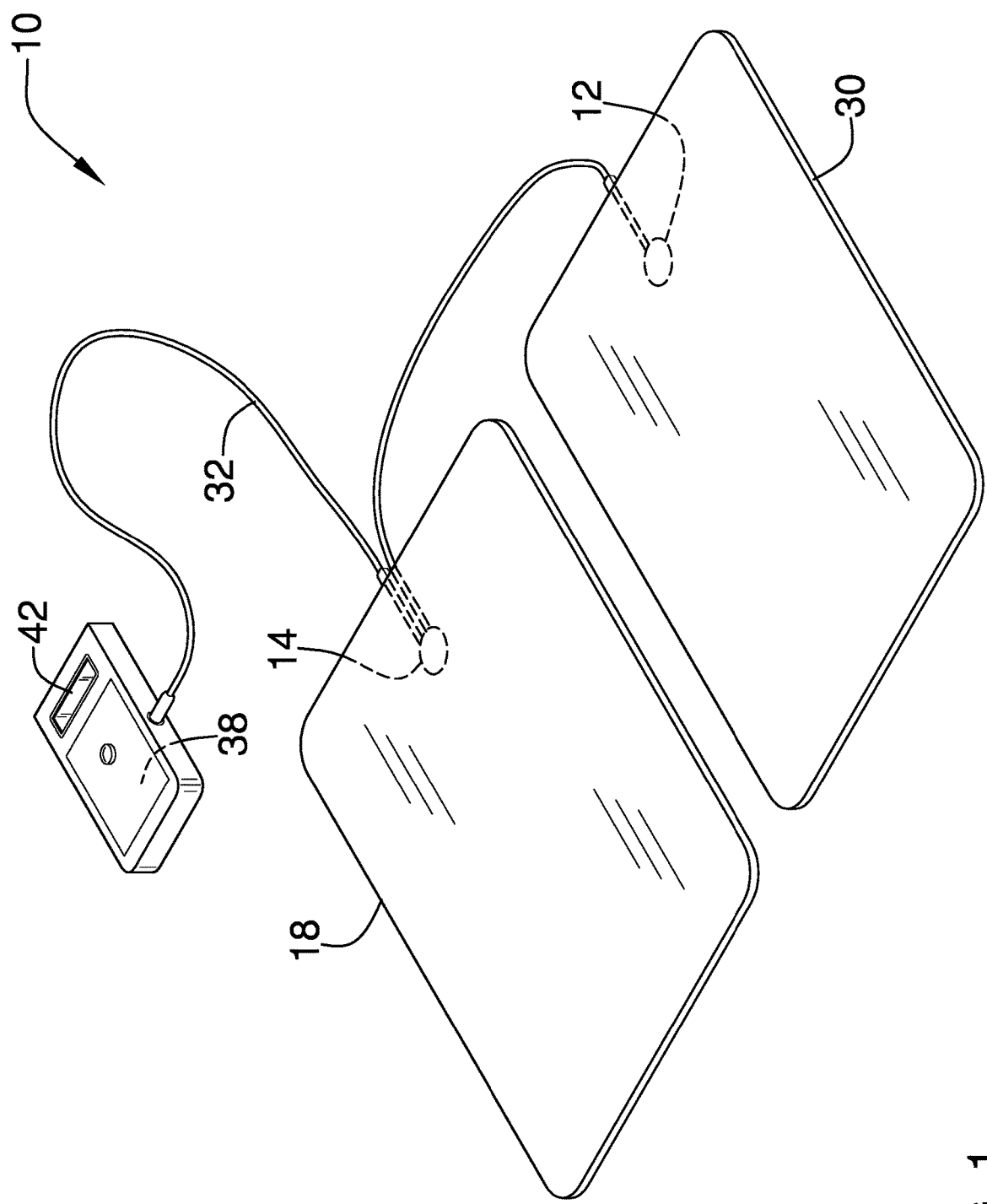
FIG. 1 is an isometric perspective view of a jump height measuring device according to an embodiment of the disclosure.

With reference now to the drawings, and in particular to FIGS. 1 through 9 thereof, a new performance measuring device embodying the principles and concepts of an embodiment of the disclosure and generally designated by the reference numeral 10 will be described.

As best illustrated in FIGS. 1 through 9, the jump height measuring device 10 generally comprises a detector 12 and a microphone 14, which are communicatively engaged to a microcontroller 16. The detector 12 is positionable on a surface such that it can detect feet of a user upon the surface and is configured to communicate a first signal to the microcontroller 16 upon the feet of the user leaving the surface. The microphone 14 is attached to a landing mat 18, which also is positionable on the surface proximate to the detector. The microphone 14 is configured to detect a sound of the feet of the user landing upon the landing mat 18 and to communicate a second signal to the microcontroller 16. The present invention also anticipates the microphone 14 being substituted by other detection means, such as, but not limited to, accelerometers, such as a piezoelectric accelerometer that is configured to sense vibration, strain gauges, gyroscopes, or the like. The microphone 14 may be positioned within or under the landing mat 18 to ensure that ambient sounds are not easily captured by the microphone 14.

The microcontroller 16 is programmed to calculate a height of a jump based upon a difference in time between receipt of the first signal and receipt of the second signal. The microcontroller 16 calculates the height of the jump using the formula $h=(1/2)gt^2$, wherein h is the height of the jump, g is the standard acceleration due to gravity, and t is the interval between the receipt of the first signal and the receipt of the second signal. The present invention is anticipated to be useful to coaches, trainers, scouts, and the like, who routinely travel to different locations, such as training camps, to evaluate athletes. The user can accurately measure an athlete's jump height and can evaluate a number of athletes without introducing bias or inaccuracy. The jump height measuring device 10 also allows an athlete to measure his own jump height.

Figure 2:
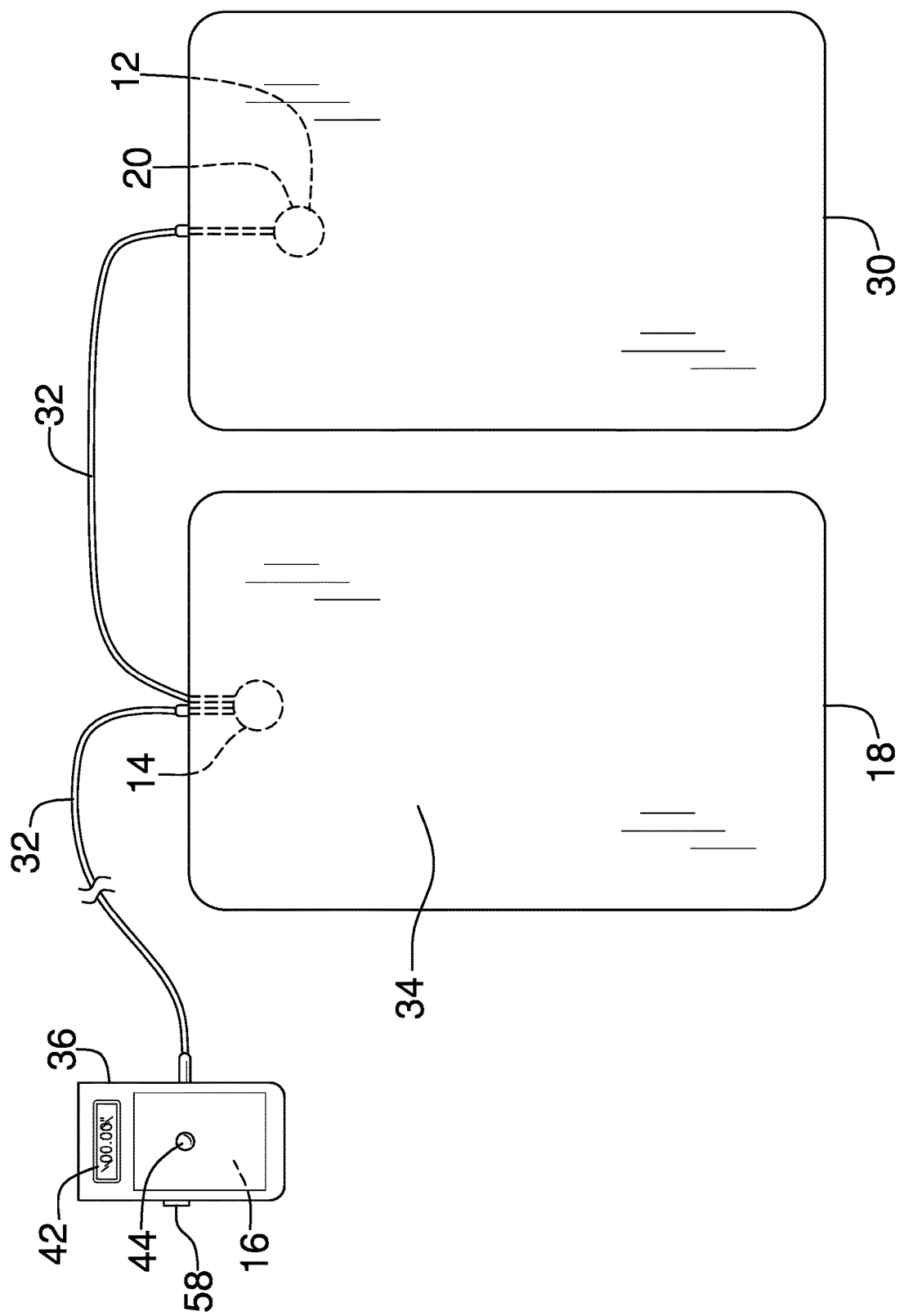
FIG. 2 is a top view of an embodiment of the disclosure.
Figure 3:
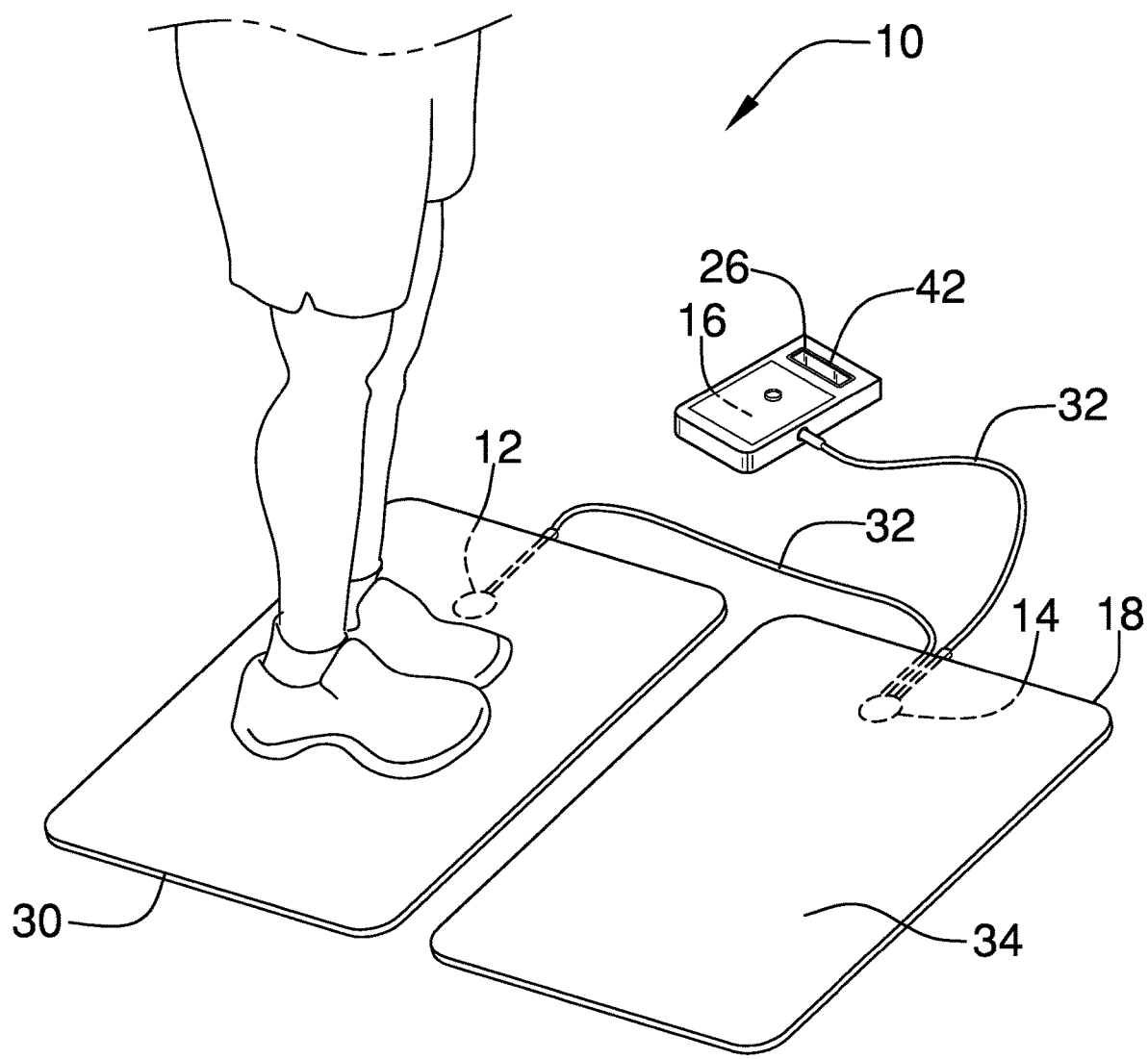
FIG. 3 is an in-use view of an embodiment of the disclosure.
Figure 4:
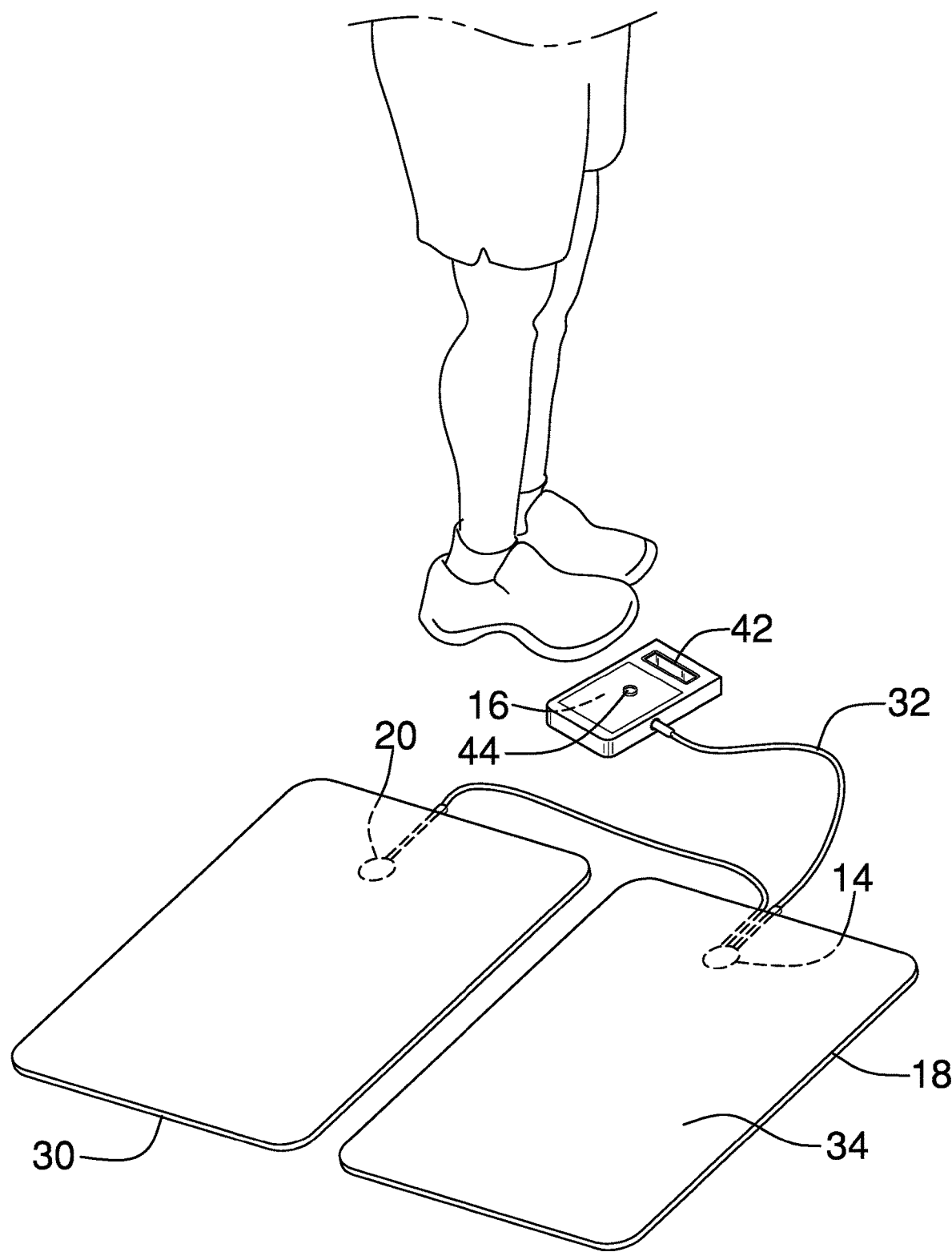
FIG. 4 is an in-use view of an embodiment of the disclosure.

The present invention anticipates the microphone 14 being miniaturized, the detector 12 comprising a tactile switch 20, and the landing mat 18 comprising rigid or semirigid plastic. Additionally anticipated is the tactile switch 20 being attached to a launch mat 30, as is shown in FIGS. 1 and 2. The launch mat 30 also would comprise rigid or semirigid plastic and would enable the tactile switch 20 to be actuated even if a foot of the user was not positioned directly over the tactile switch 20. As such, the jump height measuring device 10 would be exceptionally lightweight and compact, and thus readily transportable. While the landing mat 18 and the launch mat 30 are depicted in FIGS. 1-4 as separate mats, they also could comprise a single unitary mat.

The present invention also anticipates the microcontroller 16 being programmed to evaluate a succession of jumps and to calculate the Explosive Leg Power Force (ELPF) of an athlete, in particular a basketball player. The microcontroller 16 would determine times for each jump (hang times) and the times between the jumps (ground time) and then calculate ELPF by dividing the hang time by the ground time. A height for each jump and an average height of the jumps could be computed. The microcontroller 16 also could calculate average ground time and the average ELPF. Coaches would appreciate the ability to quantify hang time, ELPF, and jump height because each is variable between athletes and can be used to determine how best to employ the athlete or to improve the athlete's skills.

Another programming mode for the microcontroller 16 that is anticipated by the present invention would enable the jump height measuring device 10 to assess reaction time of an athlete. The microcontroller 16 would be programmed to accept a third signal from the microphone 14 that is produced by a command, such as from a starting gun, a verbal command, or the like, and to calculate a response time for the user to respond to the command. The response time would be calculated as a difference between the third signal and the first signal and may include an adjustment for the distance between the user and the microphone 14, should the microphone 14 be positioned distal from the user.

Figure 5:
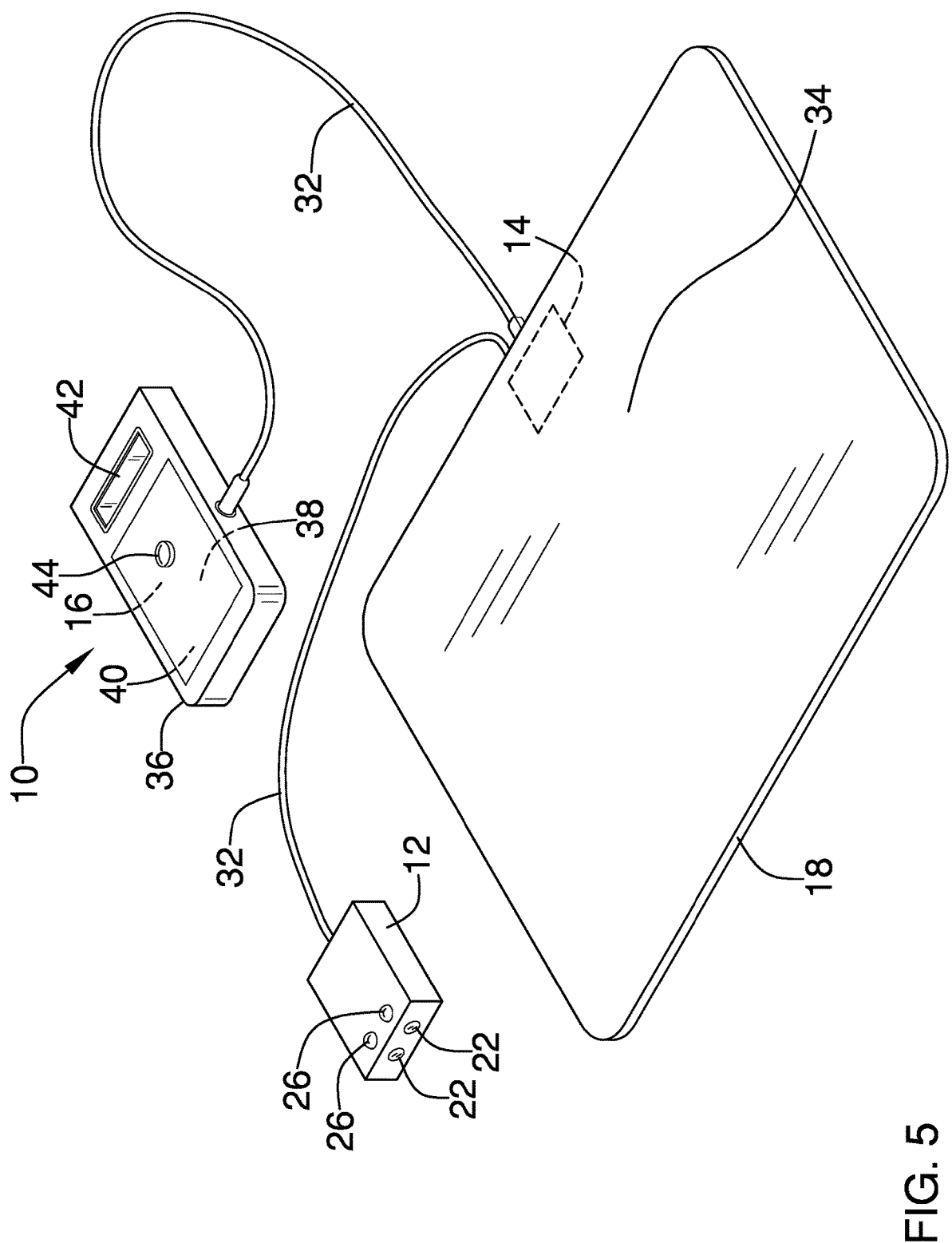
FIG. 5 is an isometric perspective view of an embodiment of the disclosure.
Figure 6:
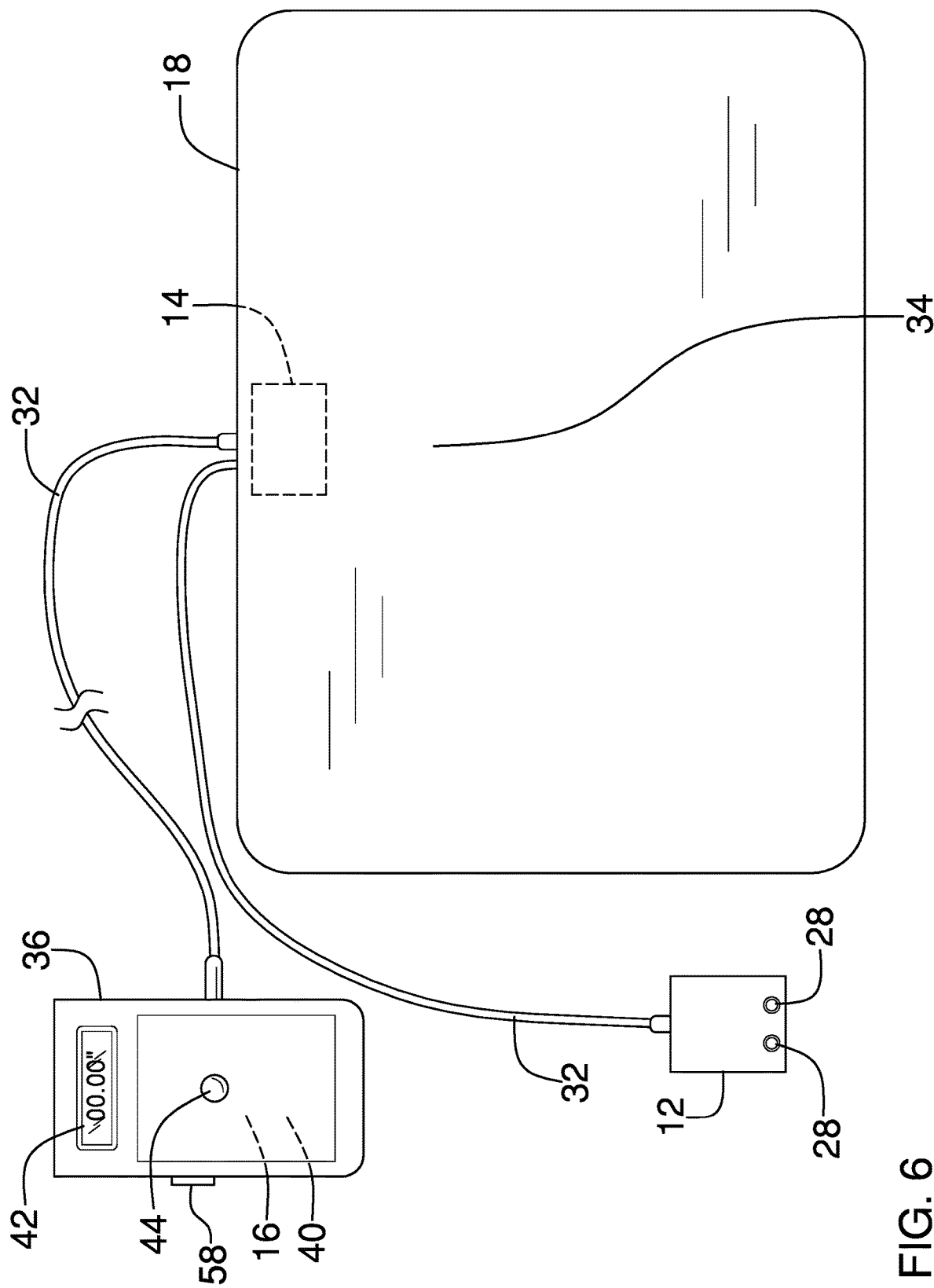
FIG. 6 is top view of an embodiment of the disclosure.
Figure 7:
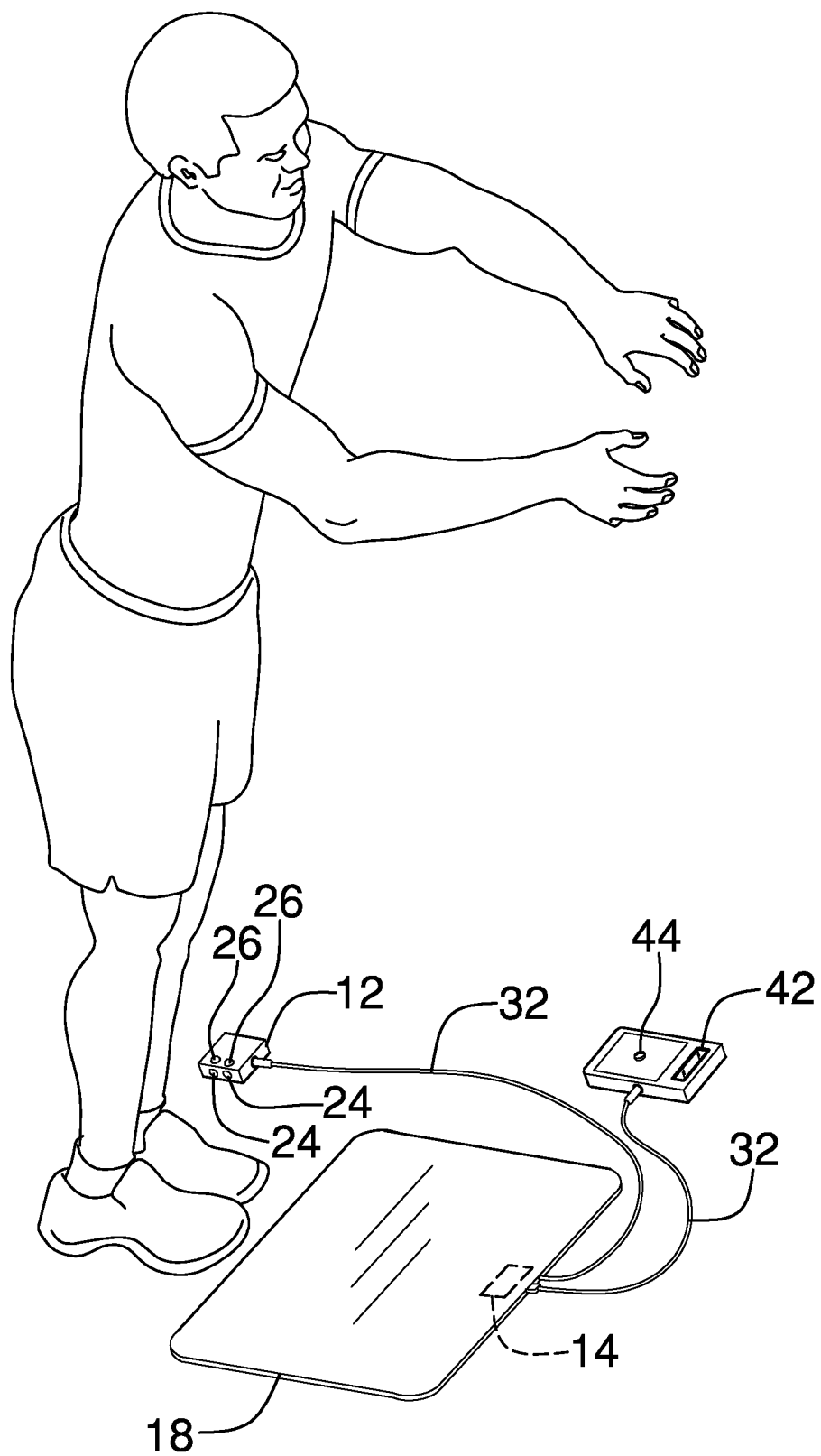
FIG. 7 is an in-use of an embodiment of the disclosure.
Figure 8:
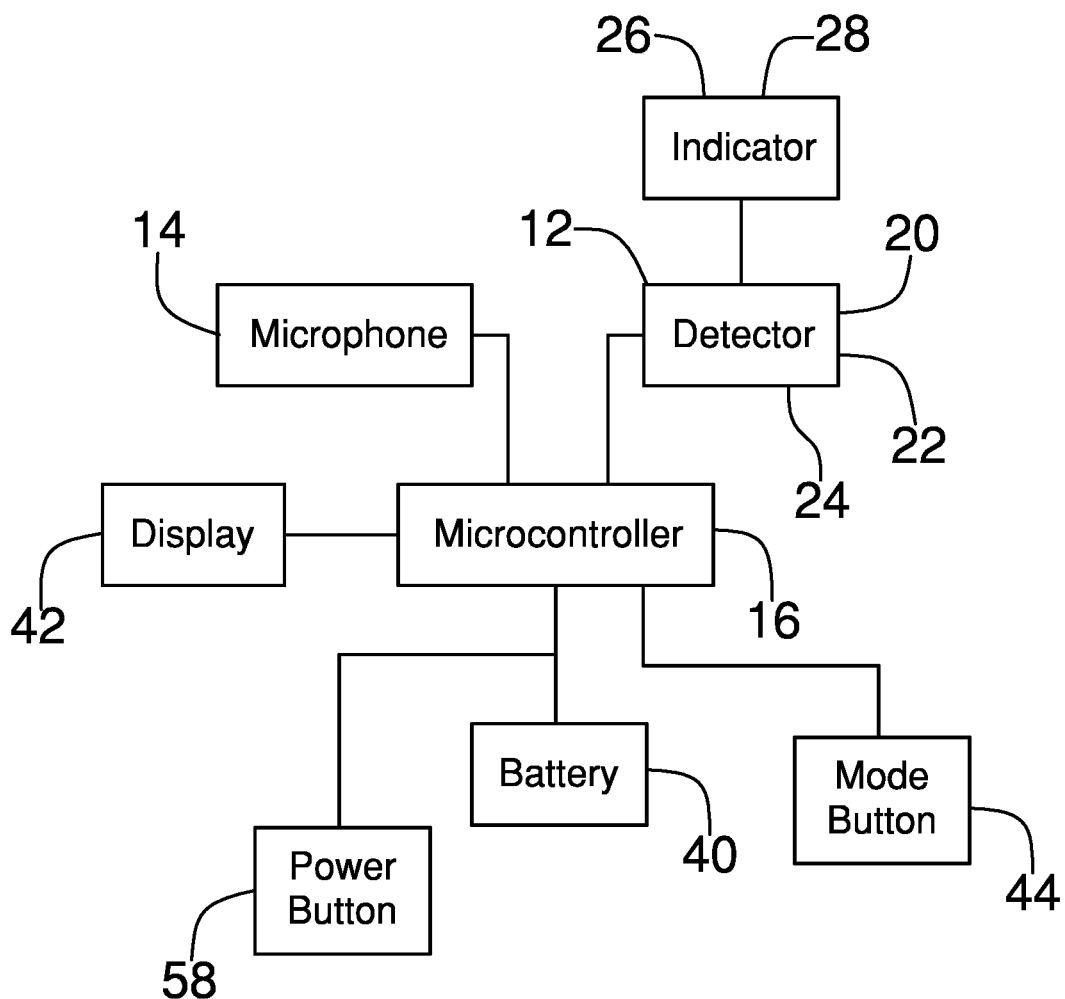
FIG. 8 is a block diagram of an embodiment of the disclosure.
Figure 9:
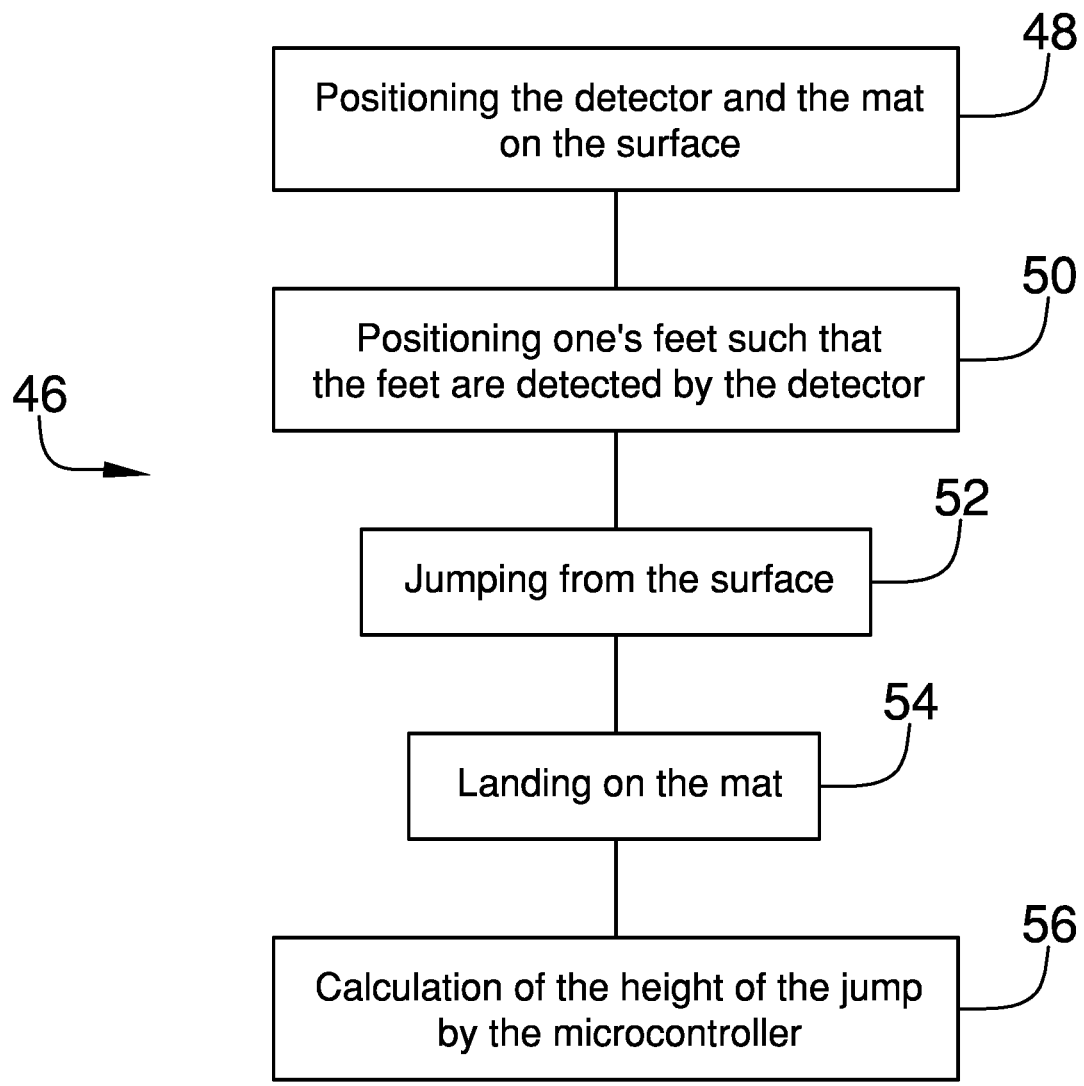
FIG. 9 is a flow diagram for a method utilizing an embodiment of the disclosure.

In another embodiment, the detector 12 comprises a proximity sensor 22, such as an infrared emitter-receiver device 24, as is shown in FIGS. 5-7. The present invention also anticipates the detector 12 comprising other detection means, such as, but not limited to, laser proximity sensors, ultrasonic sensors, or the like. The jump height measuring device 10 also may include an indicator 26, which is configured to notify the user when the feet of the user are detected by the detector 12. The indicator 26 may comprise a set of light emitting diodes 28, as is shown in FIG. 6, wherein the set of light emitting diodes is attached to the infrared emitter-receiver device 24, or other indicating means, such as, but not limited to, a speaker or the like.

The detector 12 and the microphone 14 are communicatively engaged to the microcontroller 16 by means of one or more signaling cables 32. For example, FIGS. 1 and 2 show the tactile switch 20 and the microphone 14 being connected in series to the microcontroller 16 using a single signaling cable 32. Additionally anticipated by the present invention is the proximity sensor 22 and the tactile switch 20 being interchangeably couplable to the microcontroller 16 using connectors well known to those skilled in the art of device connections.

The present invention also anticipates one or both of the detector 12 and the microphone 14 being operationally engaged to a transmitter and the microcontroller 16 being equipped with a receiver, thereby allowing for wireless transmission of one or both of the first signal and the second signal from the detector 12 and the microphone 14, respectively, to the microcontroller 16, which in this instance could comprise a smartphone (not shown). Thus configured, the jump height measuring device 10 could be used as a timing device to assess athletic performance in running sprints, hurdles, or the like, with the detector 12 being positioned at a starting position and the microphone 14 being positioned at a finishing position.

The landing mat 18 is nonplanar so that at least a portion 34 of the landing mat 18 is separated from the surface. The landing mat 18 could be pleated or creased and thus foldable. Contacting of the at least a portion 34 of the landing mat 18 with the surface upon landing of the feet of the user upon the landing mat 18 generates the sound that is detected by the microphone 14.

The microcontroller 16 is attached to a housing 36 and is positioned in an interior space 38 that is defined by the housing 36. With the detector 12 comprising a proximity sensor 22, the present invention also anticipates the proximity sensor 22 being integral to the housing 36. A battery 40 is attached to the housing 36, is positioned in the interior space 38, and is operationally engaged to the microcontroller 16. The battery 40 thus can power the microcontroller 16, the detector 12, and the microphone 14. A display 42, which is attached to the housing 36 and which is operationally engaged to the microcontroller 16, is configured to present the height of the jump. The display 42 also can function as the indicator 26, such as by displaying "Ready to Jump". The present invention also anticipates a speaker (not shown) which is attached to the housing 36 and which is operationally engaged to the microcontroller 16. The speaker would broadcast the height of the jump.

A mode button 44 is attached to the housing 36 and is operationally engaged to the microcontroller 16. The mode button 44 can be pushed by the user to select a mode of operation of the jump height measuring device 10, such as for measuring jump heights, timing of sprints, or the like.

A power switch 58 is attached to the housing 36 and is operationally engaged to the microcontroller 16 and the battery 40. The power switch 58 can be selectively switched to power on the jump height measuring device 10.

In use, the jump height measuring device 10 enables a method of measuring vertical jump height of a user 46. The method 46 entails providing the jump height measuring device 10 of claim 1. A first step 48 of the method 46 is positioning the detector 12 and the landing mat 18 on the surface. A second step 50 of the method 46 is positioning one's feet such that they are detected by the detector 12. A third step 52 of the method 46 is jumping from the surface so that the feet of the user leaving the surface is detected and the first signal is sent to the microcontroller 16. A fourth step 54 of the method 46 is landing on the landing mat 18 so that the sound of the landing is detected by the microphone 14 and the second signal is sent to the microcontroller 16. A fifth step 56 of the method 46 is calculation by the microcontroller 16 of the height of the jump based upon the difference in time between the receipt of the first signal and the receipt of the second signal. It should be understood that the above allows for usage of a single mat or two mats. Thus, a person could launch and land on the same mat or launch from one and land an or adjacent to another, wherein both the detector and microphone would be positioned with the single mat if only one mat was utilized.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A jump height measuring device comprising:
   a microcontroller;
   a detector communicatively engaged to the microcontroller and being positionable on a surface such that it can detect feet of a user upon the surface, the detector being configured to communicate a first signal to the microcontroller upon the feet of the user leaving the surface;
   a landing mat positionable on the surface proximate to the detector;
   a microphone attached to the landing mat and being communicatively engaged to the microcontroller, the microphone being configured to detect a sound of the feet of the user landing upon the landing mat and to communicate a second signal to the microcontroller; and
   the microcontroller being programmed to calculate a height of a jump based upon a difference in time between receipt of the first signal and receipt of the second signal.

2. The jump height measuring device of claim 1, wherein the detector comprises a tactile switch.

3. The jump height measuring device of claim 1, wherein the detector comprises a proximity sensor.

4. The jump height measuring device of claim 3, wherein the detector comprises an infrared emitter-receiver device.

5. The jump height measuring device of claim 1, further including an indicator operationally engaged to the microcontroller and being configured to notify the user when the detector is detecting the feet of the user.

6. The jump height measuring device of claim 3, further including an indicator operationally engaged to the microcontroller and being configured to notify the user when the proximity sensor is detecting the feet of the user, the indicator comprising a set of light emitting diodes.

7. The jump height measuring device of claim 1, further including one or more signaling cables extending between the microcontroller, the detector, and the microphone, such that the detector and microphone are communicatively engaged to the microcontroller.

8. The jump height measuring device of claim 1, further including the tactile switch being mounted to a launch mat.

9. The jump height measuring device of claim 1, wherein the landing mat comprises rigid or semirigid plastic, the landing mat being nonplanar, such that at least a portion of the landing mat is separated from the surface and such that contacting of the at least a portion of the landing mat with the surface upon landing of the feet of the user upon the landing mat generates the sound detected by the microphone.

10. The jump height measuring device of claim 1, further including:
    a housing defining an interior space, the microcontroller being attached to the housing and positioned in the interior space;
    a battery attached to the housing, positioned in the interior space, and operationally engaged to the microcontroller; and
    display attached to the housing and operationally engaged to the microcontroller, wherein the display is configured to present the height of the jump.

11. The jump height measuring device of claim 1, wherein the microcontroller is programmed to calculate Explosive Leg Power Force for a user from heights of a series of jumps and times on the surface between the jumps.

12. The jump height measuring device of claim 1, wherein the microcontroller is programmed to accept a third signal from the microphone generated by a command and to calculate a response time for the user to respond to the command, the response time being calculated as a difference between the third signal and the first signal.

13. A method of measuring vertical jump height of a user, the method comprising providing the jump height measuring device of claim 1, and:
    positioning the detector and the landing mat on the surface;
    positioning one's feet such that the feet are detected by the detector;
    jumping from the surface, such that the feet of the user leaving the surface is detected and the first signal is sent to the microcontroller;
    landing on the landing mat, such that the sound of the landing is detected by the microphone and the second signal is sent to the microcontroller; and
    calculation by the microcontroller of the height of the jump based upon the difference in time between the receipt of the first signal and the receipt of the second signal.

14. The method of claim 13, wherein the detector comprises a tactile switch.

15. The method of claim 14, wherein the detector comprises a proximity sensor.

16. The method of claim 15, wherein the detector comprises an infrared emitter-receiver device.

17. The method of claim 13, further including the tactile switch being mounted to a launch mat.

18. The method of claim 12, further including one or more signaling cables extending between the microcontroller, the detector, and the microphone, such that the detector and the microphone are communicatively engaged to the microcontroller.

19. The method of claim 12, wherein the landing mat comprises rigid or semirigid plastic, the landing mat being nonplanar, such that at least a portion of the landing mat is separated from the surface and such that contacting of the at least a portion of the landing mat with the surface upon landing of the feet of the user upon the landing mat generates the sound detected by the microphone.

* * * * *